United States Patent [19]

Neri et al.

[11] 4,448,889
[45] May 15, 1984

[54] FLUID ANALYSIS

[75] Inventors: Bruce P. Neri, North Andover; Stanley M. Liffmann, Methuen, both of Mass.; Carolyn Bergkuist, Hampstead, N.H.

[73] Assignee: Instrumentation Laboratory Inc., Lexington, Mass.

[21] Appl. No.: 389,895

[22] Filed: Jun. 18, 1982

[51] Int. Cl.³ ..................... G01N 33/20; G01N 33/52
[52] U.S. Cl. ......................................... 436/74; 436/8; 436/79; 436/166
[58] Field of Search .................. 436/74, 79, 164, 166, 436/8; 356/36

[56] References Cited

U.S. PATENT DOCUMENTS

| | | | |
|---|---|---|---|
| 3,121,613 | 2/1964 | Bittner | 23/230 |
| 3,457,045 | 7/1969 | Fraguada et al. | 23/230 |
| 3,754,865 | 8/1973 | Gindler | 23/230 |
| 3,771,961 | 11/1973 | Denney | 23/230 |
| 3,798,000 | 3/1974 | Helger | 23/230 |
| 3,822,116 | 7/1974 | Morin | 23/230 |
| 3,854,889 | 12/1974 | Rathje | 23/230 |
| 3,874,853 | 4/1975 | Byrnes | 436/164 X |
| 3,934,977 | 1/1976 | Cleaver | 23/230 |
| 3,938,954 | 2/1976 | Stavropoulos et al. | 23/230 |
| 4,308,027 | 12/1981 | Ceriotti | 23/230 |
| 4,329,149 | 5/1982 | Schoonover et al. | 356/36 X |

OTHER PUBLICATIONS

Olthuis et al., *Interference of Free Fatty Acids with the Determination of Calcium in Serum*, "Clinica Chimica Acta", 49 (1973), pp. 123-124.

Ladenson et al., *Multiple Myeloma and Hypercalcemia?*, "Clinical Chemistry", vol. 25, No. 10, (1979) pp. 1821-1825.

*Primary Examiner*—Arnold Turk

[57] ABSTRACT

In a method for colorimetric determination of calcium, the sample to be analyzed is mixed with a dye reagent of pH value at which that reagent does not produce a predetermined change when complexed with calcium ions; a first colorimetric measurement is made on the mixture of the sample and dye reagent; a second reagent is added to the mixture of the sample and dye reagent to shift the pH and activate the dye reagent producing the predetermined change; and then a second colorimetric measurement is made on the resulting mixture, the difference between the two colorimetric measurements being a measure of calcium in the sample.

19 Claims, No Drawings

FLUID ANALYSIS

This invention relates to the analysis of fluids, and more particularly to the measurement of the calcium content in biological fluids such as blood serum.

Accurate measurement of the calcium content of fluids such as blood serum, blood plasma, urine, cerebral spinal fluids, etc. is useful for diagnostic purposes, as well as for determining and analyzing the body's response to therapeutic measures. The element calcium exists in such fluids in free ionic form and in association with proteins, free fatty acids, and the like. Known methodologies for measuring total calcium in biological fluids include gravimetric and titrimetric methods that usually require large sample volumes, atomic absorption spectroscopy, a methodology that requires special equipment and that is too time consuming to be used in most routine clinical situations, and colorimetric methods, of both manual and automated types. For the clinical laboratory, procedures are desired which combine sufficient sensitivity and specificity with simplicity in conducting the procedures.

In general, colorimetric procedures depend on the ability of calcium to affect in some way the color or fluorescence of a dye. Interferences can occur which render such colorimetric assaying for calcium difficult. For example, certain constituents such as lipids, insoluble proteins, phosphates, magnesium, bilirubin, and hemoglobin present in such fluids can produce a masking effect or cause a reduction in the calcium which enters into the assay reaction. A number of proposals have been made to reduce those interferences but none have been totally satisfactory. For example, in order to overcome the problems associated with the presence of proteins and bilirubin, the biological fluid can be subjected to dialysis to remove those ingredients prior to the colorimetric determination of calcium concentration. This is a time consuming procedure and can lead to added expense as well as introduce potential errors in the subsequent determination of calcium concentration.

In accordance with the invention, the sample to be analyzed is mixed with a dye reagent of pH value at which that reagent does not produce a predetermined change when complexed with calcium ions; a first colorimetric measurement (sample blank) is made; a second reagent is added to the mixture of the sample and dye reagent to shift the pH and activate the dye reagent producing the predetermined change; and then a second colorimetric measurement is made, the difference between the two colorimetric measurements being a measure of the calcium in the sample. The calcium determination can be conducted manually or with automatic analyzers.

In preferred embodiments, the dye reagent is acidic and the second reagent is alkaline, the second reagent contains a buffer that tends to act like a solubilizing agent, and the dye reagent includes a surfactant which aids in obtaining correct sample blanks with turbid or lipemic samples, the amount of surfactant in the dye reagent being proportioned to the amount of the buffer in the second reagent to adjust the sample blank compensation for turbid specimens to equal approximately the excess absorbance (due to turbidity) in the final colorimetric reading. In particular embodiments, a sample volume of less than 0.1 milliliter is used with substantially equal quantities of the dye reagent and the second reagent, the quantity of each such reagent being less than fifty times the quantity of the sample.

A number of dyes that form colored complexes with calcium ions can be used including sodium alizarin sulfonate, methylthymolblue, and o-cresolphthalein complexone, o-cresolphthalein complexone being used in a preferred embodiment as one constituent of the dye reagent which also includes an agent capable of chelating magnesium ions which would otherwise interfere with calcium ion measurement, the preferred magnesium chelating agent being 8-hydroxyquinoline; a protein solubilizing agent which contains less than five parts per million calcium, a preferred solubilizing agent being octyl phenoxy polyethoxyethanol (Triton-X100) in a quantity between 0.05–5 volume percent of the dye reagent; and a mineral or organic acid such that the pH value of the dye reagent is less than 3.0, that pH in a particular embodiment being 1.5.

The second reagent in preferred embodiments is an alkaline buffer reagent that preferably has a pH between 9.8 and 11.5. The buffer may be an amphiprotic buffer or an amino alcohol buffer and preferably has a pK of about 9–11. In a particular embodiment, the buffer is 2-amino-2-methyl-1-propanol (AMP) that has a pK of 9.7 and is titrated with acid such that final pH value of the mixture of the sample and two reagents will be essentially 10.35. Also, in a particular embodiment, a sample quantity of less than fifty microliters is employed.

Preferably the first colorimetric measurement (the "sample blank") is taken with a dye reagent of a pH value at which calcium ions normally bound to protein and phosphate by charge interactions are not so bound, but at which the color characteristic interaction between calcium and the dye does not appear. The development of the color characteristic occurs almost instantaneously after the second reagent is added.

The invention provides an improved method for analyzing the calcium content of biological fluids that significantly reduces the effect of interferences, particularly from lipemia and hemolysis products, and that employs two separate pre-formulated aqueous reagents that have long term stability. The method can be performed in a rapid analysis sequence (less than one minute duration) with results of excellent precision and accuracy. In addition to being useful for calcium determinations of biological fluids, the invention is also useful for calcium determinations in other fields such as the foodstuff industry. Other features and advantages will be seen as the following description of a particular embodiment that is illustratative of the invention progresses.

DESCRIPTION OF PARTICULAR EMBODIMENT

A dye reagent is formulated to contain, in aqueous solution, the following ingredients:

| Dye Reagent | In General | Particular Embodiment |
| --- | --- | --- |
| O—Cresolphthalein complexone | 30–110 mg | 70 mg |
| 8-Hydroxyquinoline | 0.5–3.0 g | 1.4 g |
| Hydrochloric Acid (concentrated) | 2–10 g | 4.7 g |
| Triton X-100 (octyl phenoxy polyethoxyethanol) | 0.5–20 g | 4.2 g |
| Reagent Grade Water | Dilute above ingredients to a volume | |

| Dye Reagent | In General | Particular Embodiment |
|---|---|---|
| | of 1 liter | |

The dye reagent has a pH of about 1.5 and its absorbance (compared to water) is about one milliabsorbance unit.

A buffer reagent is formulated to contain, in aqueous solution, the following ingredients:

| Buffer Reagent | In General | Particular Embodiment |
|---|---|---|
| 2-Amino-2-Methyl-1-Propanol | 70–200 g | 125 g |
| Hydrochloric Acid (concentrated) | 15–50 g | 33 g |
| Potassium Cyanide | 0–2 g | 1.0 g |
| Sodium Azide | 0–1 g | 0.5 g |
| Reagent Grade Water | Dilute above ingredients to a volume of 1 liter. | |

The buffer reagent has a pH of about 10.5.

In an example of use, a sample of human serum is added to a quantity of dye reagent. The resulting mixture has a slightly yellowish tinge. An absorbance reading is taken at 575 nm wavelength to obtain a sample blank measurement. Any suitable colorimeter or spectrophotometer can be used to measure the absorbance. The buffer reagent, in quantity similar to the quantity of dye reagent, is then added to the sample-dye reagent mixture. A purple color that develops almost instantaneously is a measure of the calcium in the sample. Absorbance is again measured at 575 nm. The absorbance of a typical serum sample (about 9.6 mg. calcium/dL) - reagent mixture is about 500 milliabsorbance units. Subtracting the sample blank reading (adjusted for dilution due to added volume of buffer reagent) from the final reading provides an accurate measure of the concentration of calcium in the analyzed sample, based on a calibration curve constructed from absorbance readings taken using samples containing known amounts of calcium.

In another example, with an Instrumentation Laboratory 508 TM analyzer, a twenty-five microliter sample of human serum at 37° C. is added to 0.8 milliliter of dye reagent at 37° C. and mixed for about five seconds. Absorbance readings are then taken at 575 nm wavelength for 0.7 second to obtain the sample blank measurement. 0.8 Milliliter of the alkaline reagent is then added to the sample-dye reagent mixture. After an interval of about fourteen seconds (to insure full color development and optical stability of the mixture) absorbance is measured again at 575 nm for 0.7 second. The instrument subtracts the dilution adjusted sample blank reading from the final reading and displays a measure of the concentration of calcium in the analyzed sample, based on calibration data obtained from absorbance readings on samples containing known amounts of calcium. The IL System 508 TM analyzer is a multi-channel analyzer with an analysis cycle of about thirty-eight seconds duration.

A comparison of analysis results obtained in accordance with the invention using the IL 508 TM analyzer with results obtained with methodologies of other analyzers confirms the accuracy of the method of the invention. Eighty-four observations in accordance with the invention on patient serum samples having calcium values from 5.8 to 15.7 mg/DL had a correlation coefficient of 0.983 with the same samples analyzed with the methodology of another commercial analyzer; and one hundred thirty observations in accordance with the invention on patient serum samples having calcium values from 4.95 to 15.7 mg/DL had a correlation coefficient with the same samples analyzed with the methodology of a third commercial analyzer of 0.995. The day to day precision of calcium determinations in accordance with the invention with the IL 508 TM analyzer on a serum pool during the correlation study had a coefficient of variation of 0.977%. Degrees of lipemia, hemolysis and bilirubin were logged while analyzing samples in the correlation study, and no interferences with the calcium measurement were noted from any of those sample components. The invention thus is particularly useful in providing rapid, accurate and precise measurements of calcium in biological fluids.

While particular embodiments of the invention have been described, modifications thereof will be apparent to those skilled in the art and therefore it is not intended that the invention be limited to the particular embodiments or to details thereof and departures may be made therefrom within the spirit and scope of the invention.

What is claimed is:

1. A method for determination of calcium in a fluid sample comprising the steps of
    providing a first reagent that contains a dye which interacts with calcium ions and, when mixed with said sample at a first pH value, provides a first colorimetrically detectable value that is not a function of an interaction between calcium ions in said sample and said dye, and when mixed with said sample at a second pH value provides a second colorimetrically detectable value, said second colorimetrically detectable value being different from said first colorimetrically detectable value and being a function of an interaction between calcium ions in said sample and said dye,
    mixing said sample with said first reagent such that the resulting mixture has said first pH value,
    performing a first colorimetric measurement on said mixture of said first reagent and said sample,
    adding a second reagent to said mixture of said first reagent and said sample to shift the pH of the resulting mixture from said first pH value to said second pH value,
    performing a second colorimetric measurement on the resulting mixture, and
    determining the difference between said first and second colorimetric measurements, said difference being a measure of calcium in said sample.

2. The method of claim 1 wherein said dye is selected from the group consisting of sodium alizarin sulfonate, methylthymolblue, and cresolphthalein complexone.

3. The method of claim 1 wherein said first reagent includes a magnesium chelating agent in an amount effective to inhibit interference by magnesium in said first and second colorimetric measurements.

4. The method of claim 3 wherein said magnesium chelating agent is 8-hydroxyquinoline.

5. The method of claim 1 further comprising the step of mixing a non-ionic surfactant with said sample and first reagent in an amount effective to decrease the turbidity of said sample reagent mixture.

6. The method of claim 5 wherein said surfactant contains less than five parts per million calcium.

7. The method of claim 5 wherein the concentration of said surfactant in said mixture of said first reagent and said sample is in the range of about 0.05–5 volume percent of said first reagent.

8. The method of claim 1 wherein said first pH value is less than 3.0 and said second pH value is greater than 9.8.

9. The method of claim 8 wherein said second reagent contains an amphiprotic buffer that has a pK in the range of about 9–11.

10. The method of claim 9 wherein said buffer is 2-amino-2-methyl-1-propanol.

11. The method of claim 1 wherein a predetermined quantity of said sample is mixed with a predetermined quantity of said first reagent, and then mixed with a predetermined quantity of said second reagent, said predetermined quantities of said first and second reagent being substantially equal.

12. The method of claim 11 wherein said predetermined quantity of said sample is less than 0.1 milliliter and the said predetermined quantities of said first and second reagents are each less than fifty times the said predetermined quantity of said sample.

13. The method of claim 11 wherein said fluid is human blood serum.

14. The method of claim 11 wherein said first pH value is about 1.5 and said second pH value is about 10.35.

15. The method of claim 13 wherein said first reagent consists essentially of an aqueous solution of O-cresolphthalein complexone, 8-hydroxyquinoline, a surfactant containing less than five parts per million calcium, and an acid, said first reagent having a pH value of about 1.5; and said second reagent consists essentially of an aqueous solution of 2-amino-2-methyl-1-propanol and an acid, said second reagent having a pH value of about 10.5, the amount of said surfactant in said first reagent being proportioned to the amount of the 2-amino-2-methyl-1-propanol in the second reagent to adjust the turbidity compensation in said first colorimetric measurement to approximately the excess absorbance due to turbidity in said second colorimetric measurement.

16. The method of claim 15 wherein a predetermined quantity of said sample is mixed with a predetermined quantity of said first reagent, and after said first colorimetric measurement is performed on said mixture of said first reagent and said sample, a predetermined quantity of said second reagent is added to said mixture of said first reagent and said sample, said predetermined quantities of said first and second reagent being substantially equal and each being less than fifty times the said predetermined quantity of said sample, and said predetermined quantity of said sample being less than fifty microliters.

17. The method of either claim 1 or 16 wherein said first and second colorimetric measurements are performed at the same wavelength.

18. The method of claim 1 wherein a predetermined quantity of said sample is mixed with a predetermined quantity of said first reagent, and after said first colorimetric measurement is performed on said mixture of said first reagent and said sample, a predetermined quantity of said second reagent is added to said mixture of said first reagent and said sample, said predetermined quantities of said first and second reagent being substantially equal and each being less than fifty times the said predetermined quantity of said sample, and said predetermined quantity of said sample being less than fifty microliters.

19. The method of claim 18 wherein said fluid is human blood serum, said first reagent includes a surfactant in an amount effective to decrease the turbidity of said sample-reagent mixture, said first pH value is about 1.5 and said second pH value is about 10.35.

* * * * *